United States Patent [19]

Curl

[11] Patent Number: 4,559,451
[45] Date of Patent: Dec. 17, 1985

[54] APPARATUS FOR DETERMINING WITH HIGH RESOLUTION THE POSITION OF EDGES OF A WEB

[75] Inventor: Barry J. Curl, Southampton, England

[73] Assignee: De La Rue Systems Limited, Portsmouth, England

[21] Appl. No.: 440,588

[22] Filed: Nov. 10, 1982

[30] Foreign Application Priority Data

Nov. 13, 1981 [GB] United Kingdom ............... 8134266

[51] Int. Cl.$^4$ .................... G01B 11/04; G01N 21/00
[52] U.S. Cl. ................................. 250/560; 250/563; 250/572; 356/237; 356/431
[58] Field of Search .............. 250/560, 561, 562, 563, 250/571, 572, 548; 356/237, 238, 430, 431

[56] References Cited

U.S. PATENT DOCUMENTS

| | | | |
|---|---|---|---|
| 3,835,332 | 9/1974 | Bridges | 250/563 |
| 3,859,538 | 1/1975 | Mannonen | 250/572 |
| 4,172,666 | 10/1979 | Clarke | 250/563 X |
| 4,376,583 | 3/1983 | Alford et al. | 250/563 X |

FOREIGN PATENT DOCUMENTS

| | | |
|---|---|---|
| 1204951 | 9/1970 | United Kingdom . |
| 1387320 | 3/1975 | United Kingdom . |
| 1520693 | 8/1978 | United Kingdom . |
| 1563570 | 3/1980 | United Kingdom . |
| 197709 | 9/1977 | U.S.S.R. ............... 250/560 |

Primary Examiner—Edward P. Westin
Attorney, Agent, or Firm—Cushman, Darby & Cushman

[57] ABSTRACT

Apparatus for scanning a document includes an array of light emitting diodes, or optical fibers, arranged across the width of the document and extending further than its edges, a corresponding array of photo-diodes, or fiber optics connected to photo-diodes, for providing analog intensity signals indicative of the degree of transmission of light to each sensor, and an analyzing circuit responsive to each of the intensity signals to determine the condition of the document, and especially to determine the position of the edges of the document, and the size of any pin-holes or tears in the document. According to the invention, the analyzing circuit derives digital signals indicative of the relative intensity value of each analog signal with regard to three or more predetermined threshold values of intensity, each threshold level corresponding to a different degree of obscuration of a sensor by the corresponding area of the document. If a threshold value T3 is exceeded, but a higher threshold value T4 is not exceeded, then the circuit assumes that the corresponding sensor indicates ¼ obscuration, and that for example the edge of the document lies at a distance from the neighboring sensor equal to ¼ of the separation between adjacent sensors.

13 Claims, 10 Drawing Figures

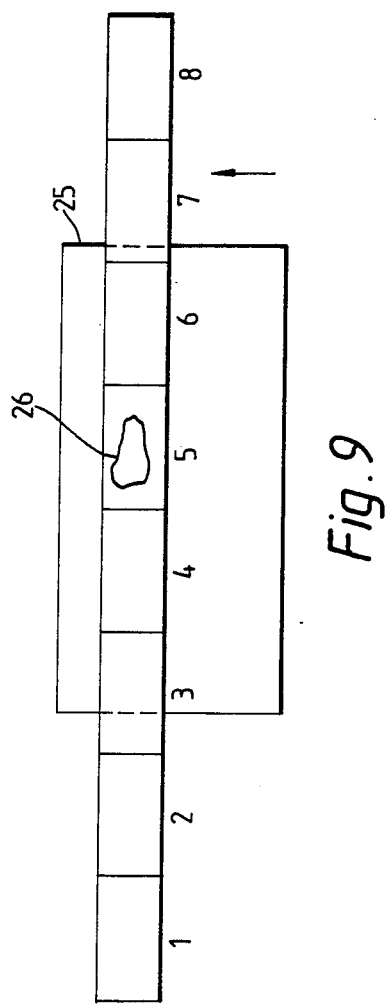

APPARATUS FOR DETERMINING WITH HIGH RESOLUTION THE POSITION OF EDGES OF A WEB

FIELD OF THE INVENTION

This invention relates to apparatus for scanning a surface to determine the position of its edges or the size of pin-holes, and is particularly useful for scanning banknotes or other documents.

BACKGROUND OF THE INVENTION

Conventional optical apparatus for detecting flaws, stains and holes in web material, such as is described in British Pat. No. 1204951, includes a plurality of photodetectors disposed in a parallel configuration to detect reflected or transmitted light from the web material. A signal from each detector is amplified in a separate channel, and the amplified signal is compared with a threshold level. The result of the comparison indicates the presence or absence of an abnormally high signal level which would indicate a flaw such as a stain or hole in the region of the web material adjacent to that detector.

This technique was refined in the apparatus of British Pat. No. 1387320, which was particularly useful for detecting stains and flaws on the surface of moving sheet metal. An amplified signal from each of an array of photodetectors was compared with two different threshold levels. If the signal exceeded the upper threshold or fell to a level below the lower threshold then the presence of a speck was assumed, for example. The outputs from each of the threshold comparators were combined at OR gates in order to determine the presence of a single speck or, using a counter to decide if a strip of metal contained too many specks.

In all known sets of optical apparatus for scanning the surface of web material, even in those which use two different threshold levels in the analysing circuit, the resolution is limited by the physical size of the photodetectors. For an array of adjacent photodetectors, the optical resolution is equal to the distance between the centers of adjacent detectors. If the light from the detected area of the surface is made to diverge before it reaches the array of photodetectors, a greater resolution could in theory be obtained. However, accurate measurements of the optical transmission factor of a web of material can only be obtained using parallel, non-divergent beams of light, and this requires that the photodetectors are as close together as are the regions on the surface which they detect. The situation can be improved with the use of optical fibers or fiber bundles, which allow the photodetectors to be stationed remotely from the surface which they detect. Nevertheless, the resolution of the system is still limited by the physical separation of adjacent optical fibres.

SUMMARY OF THE INVENTION

It is therefore an object of the present invention to provide apparatus of the type described above for scanning the surface to determine the position of its edges or of pin-holes or tears to a greater optical resolution than was previously possible.

Apparatus according to the invention for scanning a surface of a sheet or web to determine the position of faults in the sheet or web or of the edge of the sheet or web, comprises a plurality of photoelectric sensors arranged transversely across the surface to receive light from a corresponding plurality of elemental areas across a transverse strip of the surface, conveyor means for providing relative longitudinal movement of the sheet or web with respect to the sensor array, allowing the sensor array to scan the sheet or web longitudinally, and a processing circuit to determine the relationships between the signal from each sensor, representing the intensity of received light, and three or more predetermined threshold values of intensity and, in accordance with the said relationships, to determine the transverse position of any discontinuity in the amount of light received from the elemental areas across the strip, corresponding to a fault in or an edge of the sheet, to a greater resolution than would be possible using only one threshold value of intensity for each sensor.

The improvement in the resolution obtainable is by a factor equal to the number of threshold values. In the preferred embodiment of the invention four threshold values are chosen so that the degree of obscuration of each sensor can be detected to the nearest quarter of the distance separating adjacent sensors.

The apparatus preferably includes means responsive to the signal obtained from a sensor which is completely obscured by the said surface, to derive a signal indicative of the optical transmission factor of the region of the surface which is obscuring the sensor. The optical transmission factor provides an indication of the presence of soil or grease on or under the surface.

In the preferred apparatus, the processing circuit includes means responsive to the said relationships between the signals and the threshold values, to determine the position of an edge or both edges of the surface, by locating a group of adjacent sensors showing a transition from substantial obscuration to substantial transmission of light. The said relationships indicate the degree of obscuration of the sensor overlying the edge of the surface, enabling a processing circuit to determine the position of the edge with an accuracy at least as great as one third of the separation between adjacent sensors.

The presence and position of pin-holes or tears in the surface are preferably determined by the processing circuit in a manner similar to that described above for locating the edge of the surface. Where the edge of the surface is torn away, the circuit indicates a sudden shift in the apparent position of the edge of the surface.

The sensors are preferably coupled to their corresponding areas of the surface by means of optical fibers or bundles of optical fibers. The array of sensors is then constituted by a fiber optic detector head housing one end of each of the optical fibers, the opposite end of each fiber being coupled to its associated photoelectric sensor.

The illumination means preferably comprises a light source coupled to the other face of the surface by means of an array of optical fibers. Each of the optical fibers has one end coupled to the light source and the opposite end coupled to a fiber optic detector head stationed next to the surface. The fiber optic source head and the fiber optic detector head are preferably arranged on opposite sides of the surface so that parallel, non-divergent beams of light pass through the surface from each element of the source head to its associated element of the detector head. The divergence of the beams of light may be controlled with the aid of lenses interposed in the light path between the source head and the detector head.

BRIEF DESCRIPTION OF THE DRAWINGS

In order that the invention may be better understood, several embodiments of the invention will be described below with reference to the accompanying drawings, wherein:

FIG. 9 illustrates the manner in which the control signals are used.

DETAILED DESCRIPTION OF THE INVENTION

Figure 1:
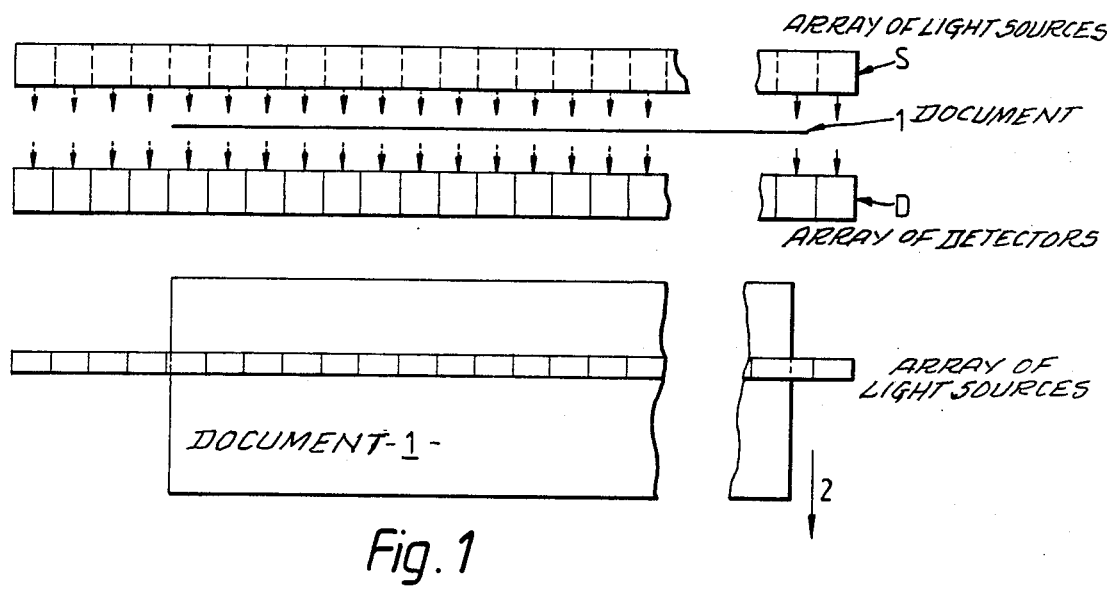
FIG. 1 shows a document passing between a source head and a detector head, the arrangement being shown both in the plane of the light beams and in the plane of the documents respectively.

The principle behind the invention is illustrated in FIG. 1, showing a document 1 intercepting the optical paths between an array of light sources S and an array of corresponding detectors D. The arrangement is shown in plan view, i.e. in the plane of the light paths perpendicular to the document, and also in side view, i.e. in the plane of the document 1. The document 1 is translated past the detectors in a direction indicated by an arrow 2.

Figure 2:
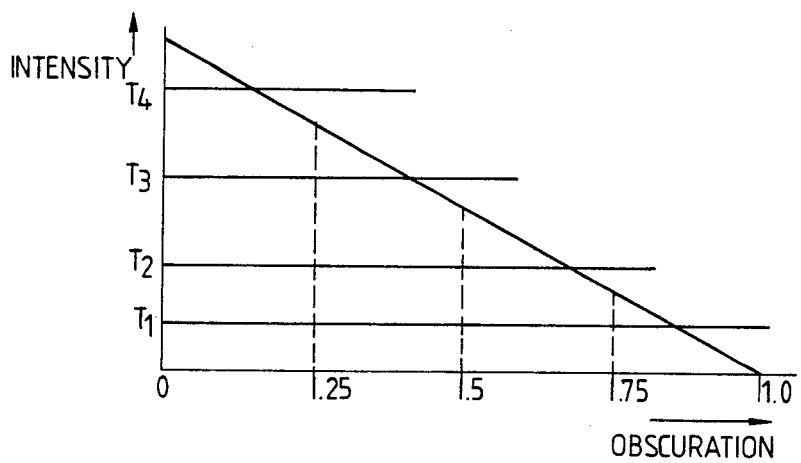
FIG. 2 is a graph showing the variation of the output level from the detector with the degree of obscuration of the detector head by a portion of the document of FIG. 1.

The output from each photodetector of the array D of photodetectors depends on the degree with which it is obscured by the document. The variation of the intensity of the output of each detector is shown as a function of the degree of obscuration of the detector in FIG. 2. It will be seen that the intensity is a linear function of the degree of obscuration. It is convenient to provide four threshold levels of intensity, shown as T1 to T4 in FIG. 2. Threshold level T1 corresponds to a detector lying between $\frac{3}{4}$ and complete obscuration. The threshold level T2 corresponds to a degree of obscuration lying between $\frac{1}{2}$ and $\frac{3}{4}$ of the complete obscuration, threshold level T3 corresponds to around $\frac{1}{3}$ obscuration, and threshold level T4 corresponds to a degree of obscuration between 0 and $\frac{1}{4}$. An analyzing circuit responsive to the output of each detector assumes, for that detector, that if the threshold level T4 is exceeded then there is no portion of the document present. The circuit also assumes that if the threshold level T1 is not exceeded, then the detector is fully obscured. For levels exceeding threshold level T1 but not exceeding T2, $\frac{3}{4}$ obscuration is assumed. For levels between T2 and T3, $\frac{1}{2}$ obscuration is assumed, and for levels between T3 and T4, $\frac{1}{4}$ obscuration is assumed.

Figure 3:
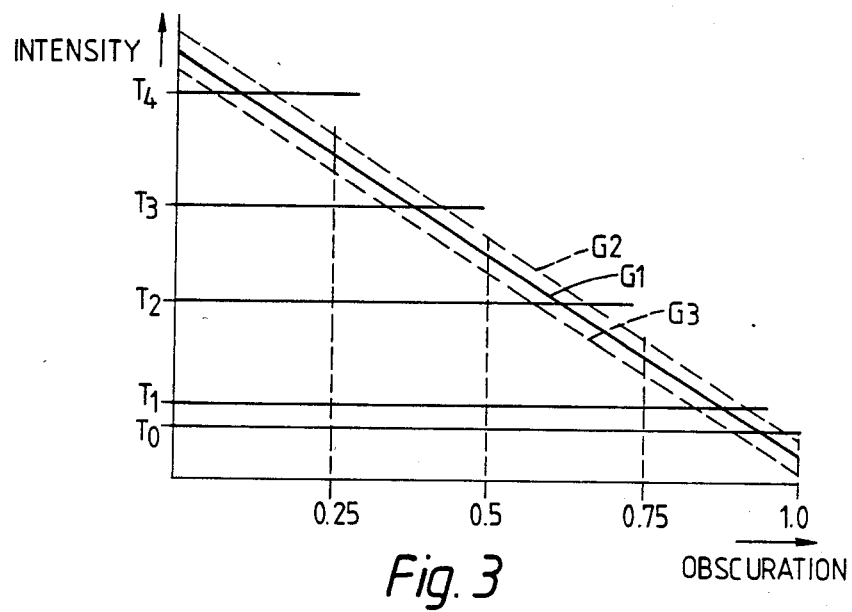
FIG. 3 is a graph similar to that of FIG. 2, showing variations of detector output with the condition of the document being scanned.

The level of the intensity detected depends on the condition of the document, as shown in FIG. 3. In this graph, G1 corresponds to the passage of a normal, new document. A greasy document transmits more light than normal, and results in a graph similar to G2. A soiled document generally transmits less light, and results in line G3. The spread between G2 and G3 depends on the wavelength of the light employed. This effect produces a limit on the ultimate resolving power of the system, that is the number of thresholds that can usefully be established, but the effect is small enough to permit a substantial improvement in resolution over previous systems using only one threshold.

Figure 4A:
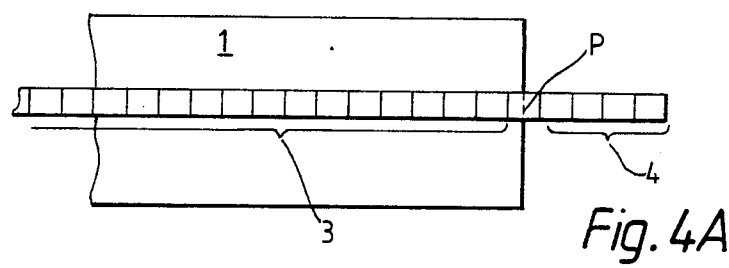
FIG. 4A illustrates the method by which the edge of a document is recognized.
Figure 4B:
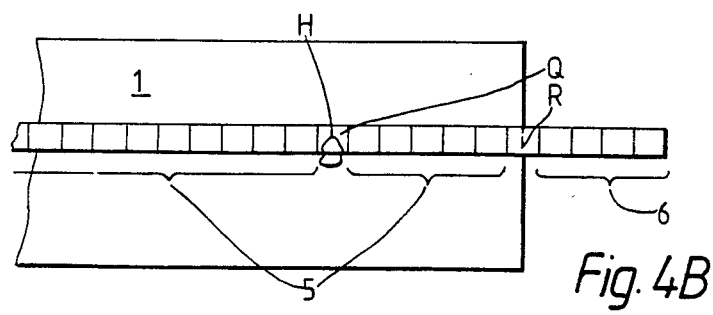
FIG. 4B illustrates the way in which both holes in the document and the edge of the document are detected by this system.

FIGS. 4A and 4B illustrate the use of individual intensity measurements from the detectors to establish the presence of holes in the document and the position of an edge of the document. In FIG. 4A, a partially obscured detector P is preceded in the sequence by a row of totally obscured detectors 3, and is succeeded by a row of unobscured detectors 4. The analyzing circuit therefore recognizes that the edge of the document lies at the detector P. Then depending on the degree of obscuration of detector P, the analysing circuit deduces the position of the edge to an accuracy of better than $\frac{1}{4}$ of the separation between adjacent detectors. For example, if threshold T3 was exceeded but T4 was not exceeded, then detector P has a nominal $\frac{1}{4}$ obscuration, and the edge of the detector is assumed to lie at a position $\frac{1}{4}$ of the way across the detector P.

The presence of a hole H is assumed where one or more partially obscured detectors are surrounded by groups 5 of totally obscured detectors, as shown in FIG. 4B. Such a partially obscured detector Q lies between groups 5 of totally obscured detectors, and its presence is deduced by the analyzing circuit. In the same figure, a partially obscured detector R is preceded by a group 5 of totally obscured detectors, and is succeeded by a group 6 of unobscured detectors; it is therefore indicative of the edge of the document.

In addition to the location of holes and edges of documents, the analyzing circuit is capable of determining the condition of the document. The intensity signal from any detector which is totally obscured by the document may be used to give an indication of the optical transmission factor (OTF) of the document. Measurement of the OTF over all or particular areas of the document is used to determine the degree of soiling of individual documents. Needless to say, the intensity signal would be below all the thresholds T1 to T4 for the purposes of this measurement.

The accuracy of the measurement of the intensity is improved by making the included angle of the light rays emanating from each source, and the acceptance angle of the corresponding detectors, as near to zero as possible. In other words, the beam of light passing through each region of the document should be ideally a parallel beam of light. Using near parallel light also enables a greater variation in the position of the document between source and detector to be tolerated; clearly, if the light is accurately parallel, the position of the interception of the beam by the document is immaterial.

Each detector is never completely obscured by the documents, due to the finite value of the OTF. This tends to limit the accuracy of the apparatus, and the limitations can be reduced by a suitable choice of the wavelength of light used. The OTF of paper documents diminishes significantly as the wavelength is reduced, and consequently the maximum level $T_o$ (FIG. 3) for completely obscured detectors is reduced. The variation between the intensities transmitted by documents of different conditions, as shown in FIG. 3, is also reduced by using light of short wavelengths.

In some situations there may be some variation in the intensity output from each detector due to phenomena unconnected with the characteristics of the documents, such as variations in the amount of light produced by each source, variations in the sensitivity of the detector, (both of which may possibly be caused by changes in the supply voltage), ageing, the deposition of dirt and dust, and general wear on the lenses and other optical components, etc. In order to retain the necessary accuracy of measurement, an amplifier for each detector of the array of detectors D can be used which has an automatic gain control system so that the detector output occurring between the passage of documents is used to set the gain of the amplifier to give a full scale output with this signal. The time constant in the gain control circuit is chosen so that only slowly varying outputs can set the gain, in order that the reduction in the output occurring when a document passes should be indicated accurately. By this method, the outputs from all the detectors are normalized to the same full scale output.

There are numerous extensions to the processing carried out by the analyzing circuit, allowing a comprehensive assessment of the document's size, shape, orientation, degree of damage, soiling and greasiness to be made.

Three types of optical system will now be described, with reference to FIGS. 5, 6 and 7.

Figure 5:
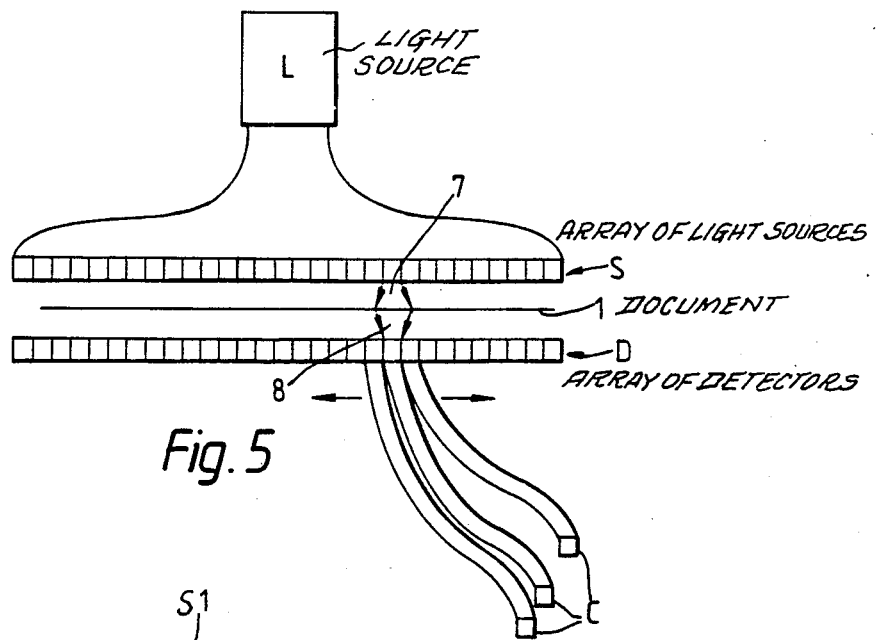
FIG. 5 shows an embodiment of the invention employing exclusively fiber optic cables.
Figure 6:
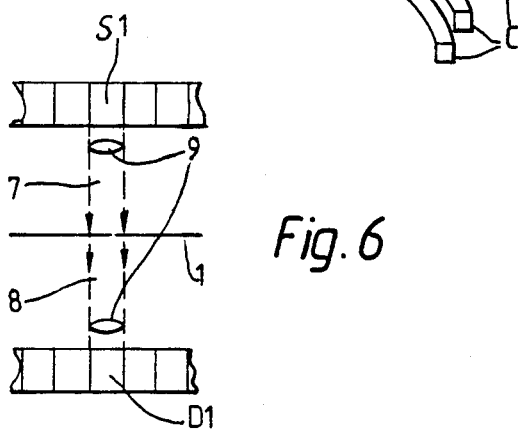
FIG. 6 shows in detail a single element of the optical system, comprising a fiber optic source, a fiber optic detector and two lenses.

In FIG. 5, a system employing fiber optics is shown. A light source L supplies light to all regions of a strip of the document 1 by means of an optical fiber fishtail array, the ends of the optical fibers constituting the array S of sources. Each optical fiber provides a slightly divergent source beam 7, with a finite included angle. The array of detectors D consists of the ends of identical optical fibers, the other ends of each of the optical fibers being connected to an equal number of photocells C. For each channel of light through the document, there is an optical fiber for providing the light, an optical fiber for collecting the light, and a photocell C for producing an intensity signal. The acceptance angle of the reception optical fibers, whose ends are held in the array of detectors D is generally equal to the divergence angle of light emanating from the source fibers. A converging beam of light 8 is thus collected by each reception fiber. The angle of light emanating from the source fibers and the acceptance angle of the reception of fiber is fixed by the refractive indices of the core and of the cladding of the individual fibers. This angle can be reduced by making a suitable choice of materials, and is preferably not larger than 20°. Alternatively, as shown in the arrangement of FIG. 6, small lenses can be placed at the ends of each of the fibers to reduce these angles to suitable values. In FIG. 6, a single light channel is shown, comprising the end S1 of a source fiber, the end D1 of a reception fiber, and the two interposed lenses 9.

Figure 7:
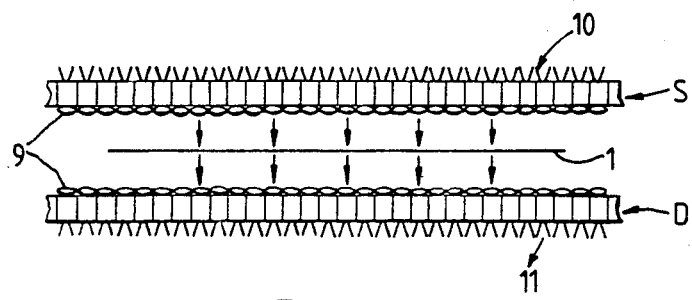
FIG. 7 shows a further embodiment of the invention, using assemblies of light emitting diodes and photodiode detectors in place of the fiber optics of FIGS. 5 and 6.

An alternative system is shown in FIG. 7, which does not use fiber optics, but places the lenses 9 adjacent to an array of light emitting diodes and also to an array of photo-diodes. The light emitting diodes constitute the array of light sources S, and are individually connected to power sources via wires 10. The photodiodes constitute the array of detectors D, and are individually connected by wires 11 to the analyzing circuit.

With any of these optical systems, the use of light of lower wavelengths reduces the effect of variations in the OTF. The accuracy of the measurement of the OTF is improved by using parallel or near parallel light. Also with any of these optical systems, the analyzing circuit may scan across the illuminated strip of the document 1 by analyzing each of the intensity signals from the detectors in turn, in a/cyclic arrangement. However, it is not necessary to scan in this manner, and the intensity signals from all of the detectors may be processed simultaneously. With either method, once the analyzing circuit has received intensity signals from all the detectors, it proceeds to analyze the condition of the document, and to detect the presence of holes or tears, and the position of the edge of the document, etc. Successive determinations of the position of the edge of the document may be used to deduce any error in the orientation of the document. For example, if the position of the edge changes slightly as the document is moved past the detectors, the edge is assumed to be slightly skew. The dimensions of the document may be determined by detecting the positions of opposite edges of the document in the manner described above. The width of the document in the direction in which it is moved past the detectors, may be determined by considering the speed of its motion past the detectors and the time for which it obscures some of the detectors.

Figure 8:
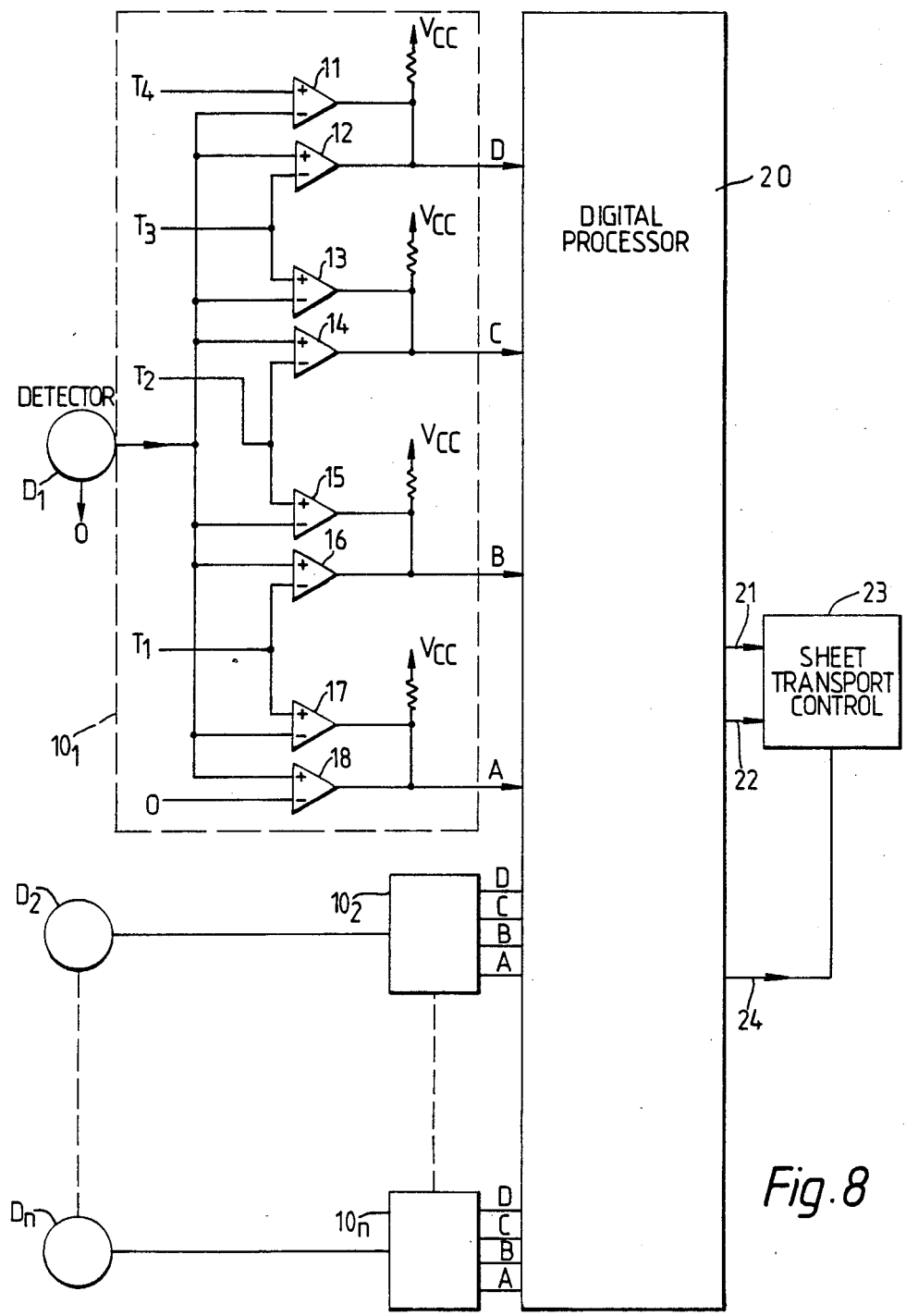
FIG. 8 shows a circuit responsive to detector outputs to provide control signals.

In FIG. 8, signals from the detectors $D_1, D_2 \ldots D_n$ are applied to threshold comparator units $10_1, 10_2 \ldots 10_n$. Only the comparator unit $10_1$ is shown in detail in this comparator unit, signals from the detector are applied to each of eight comparators 11, 12, 13 . . . 18. The detector signals are applied to the inverting channels of the odd-numbered comparators and to the non-inverting channels of the even-numbered comparators. Four threshold level signals $T_1$ to $T_4$ are generated, in addition to the zero level signal. The threshold level signal $T_4$ is applied to the non-inverting input of comparator 11; $T_3$ is applied to the inverting input of comparator 12 and the non-inverting input of comparator 13; $T_2$ is applied to the inverting input of comparator 14 the non-inverting input of comparator 15; and $T_1$ is applied to the inverting input of comparator 16 and the non-inverting input of comparator 17; and the zero level signal is applied to the inverting input of comparator 18. The outputs of comparators 11 and 12 are connected in common through a resistor to the supply Vcc and provide the output signal D of the threshold comparator unit. Similarly, the remaining comparator outputs are connected in pairs to provide the output signals C, B and A. Each comparator causes its output to be grounded if the voltage at its non-inverting input is lower than that on its inverting input; in the other condition, its output is open-circuit. The comparator outputs are connected together in pairs so that if the sensor output lies between zero and $T_1$, then $A=1$, $B=0$, $C=0$ and $D=0$. If the sensor output lies between $T_1$ and $T_2$, then $A=1$, $B=1$, $C=0$, $D=0$; and so on. The four outputs B, C, D and A from each of the sensors are applied to a digital processor 20, which analyzes the signals and provides an output on conductor 21 if the document is under a width limit and an output on line 22 if the document is over another width limit. The signals on lines 21 and 22 are applied to a sheet transport control 23, which diverts the sheets from the normal flow path if necessary.

A further output on line 24 indicates the size of a fault found in the document.

FIG. 9 illustrates how the signal analysis is carried out. The boxes 1 to 8 represent an array of eight detectors. A document 25 containing a hole 26 is being fed past these detectors. In the example shown, detectors 1, 2 and 8 are not obscured, detector 3 is 60% obscured and detector 7 is about 12% obscured, sensors 4 and 6 are 100% obscured, and sensor 5 is only partially obscured owing to the presence of the hole 26 in the document.

The processor circuit 20 ascertains that the edges of the document occur in positions 3 and 7, because all detectors outside detectors 3 and 7 (i.e., 1, 2 and 8) are unobscured and although detector 5 is only partially obscured, it has obscured detectors on each side. Furthermore, the processor ascertains the positions of the edges of the sheet more precisely because of the four thresholds. If the four thresholds used are at equal intervals, the width of the document would be estimated at $(\frac{3}{8}+1+1+1+\frac{1}{8})=3\frac{1}{2}$ detector pitches. It will be appreciated that the center value of each threshold subdivision is $\frac{1}{8}$, $\frac{3}{8}$, $\frac{5}{8}$ and $\frac{7}{8}$ of a full cell.

The processor decides whether this width is over or under preset width limits and it sends the signals to the document transport control 23, to control the destination of the sheet accordingly.

The degree of obscuration of detector 5 indicates the size of the hole and again may be used to control the sheet transport so that any document with two large a hole is diverted out of the flow path.

I claim:

1. An apparatus for scanning a surface of a sheet like member to determine the position of edges of the member, said apparatus comprising:
   a sensor array consisting of a plurality of photoelectric sensors arranged transversely across the surface to receive light from a corresponding plurality of elemental areas across a transverse strip of the surface,
   conveyor means for providing relative longitudinal movement of the member with respect to the sensor array, allowing the sensor array to scan the member longitudinally, and
   a processing circuit for determining the relationships between the signal from each sensor, representing the intensity of received light, and at least three predetermined threshold values of intensity and, in accordance with said relationships, for determining the transverse position of a discontinuity in the amount of light received from the elemental areas across the strip, corresponding to an edge of the member, to a greater resolution than would be possible using only one threshold value of intensity for each sensor.

2. An apparatus in accordance with claim 1, including a source of light for transmitting light through the elemental areas into corresponding ones of the sensors, the light source extending transversely beyond at least one edge of the member thereby to transmit light directly to corresponding sensors.

3. An apparatus in accordance with claim 1, wherein the number of threshold levels is four, so that the transverse position of any discontinuity is detected to the nearest quarter of the distance separating adjacent sensors.

4. An apparatus in accordance with claim 1, including means responsive to the signal obtained from a sensor which is completely obscured by the member, to derive a signal indicative of the optical transmission factor of the region of the surface which is obscuring the sensor.

5. An apparatus in accordance with claim 1, wherein the processing circuit includes means responsive to the said relationships between the signals and the threshold values, to determine the position of at least one of the surface, by locating a group of adjacent sensors showing a transition from substantial obscuration to substantial transmission of light.

6. An apparatus in accordance with claim 5, wherein the processing circuit further includes means responsive to said relationships between the signals and the threshold values, to determine the position of the edge within the boundaries of the partially obscured sensor, by taking account of which threshold values are exceeded by the level of the signal derived from the partially obscured sensor.

7. An apparatus in accordance with claim 5, wherein the processing circuit includes means responsive to the said relationships to determine the position of any one of a pinhole and a tear in the surface, by determining which sensors are surrounded by groups of substantially obscured sensors.

8. An apparatus in accordance with claim 7, wherein the processing circuit determines the size of the pinhole or tear within the boundaries of the partially-obscured sensor which receives light through the pin-hole or tear, by taking account of which threshold values are exceeded by the level of the signal derived from the partially-obscured sensor.

9. An apparatus in accordance with claim 1, wherein the sensors are coupled to corresponding areas of the surface by means of optical fibers.

10. An apparatus in accordance with claim 2, wherein the light source is coupled to the opposite face of said surface by means of an array of optical fibers.

11. An apparatus in accordance with claim 2, wherein light passing between the light source and the sensors is transmitted through the member in substantially parallel beams.

12. An apparatus in accordance with claim 1, wherein said transverse strip is illuminated by an array of light-emitting diodes, and each sensor is a photo-diode arranged to receive light from a corresponding one of the light-emitting diodes.

13. An apparatus in accordance with claim 10, further including converging lenses interposed in the light paths between elements of the light source and their corresponding sensors, for the purpose of forming a substantially parallel beam of light.

* * * * *